United States Patent [19]

Wightman

[11] Patent Number: 5,570,030
[45] Date of Patent: Oct. 29, 1996

[54] MOISTURE SENSOR AND CONTROL SYSTEM

[76] Inventor: William E. Wightman, 11 Village Dr., Littleton, Colo. 80123

[21] Appl. No.: 423,555

[22] Filed: Apr. 17, 1995

Related U.S. Application Data

[63] Continuation-in-part of Ser. No. 57,871, May 7, 1993, abandoned.

[51] Int. Cl.⁶ ............................................. G01R 27/26
[52] U.S. Cl. ..................... 324/694; 324/724; 324/715; 137/78.5
[58] Field of Search ........................... 324/715, 724, 324/664, 694; 361/280, 281; 137/78.5; 73/73; 340/602

[56] References Cited

U.S. PATENT DOCUMENTS

| | | |
|---|---|---|
| 2,636,962 | 4/1953 | Bouyoucos et al. . |
| 2,754,478 | 7/1956 | Goldsmith ............................. 361/280 |
| 2,768,028 | 10/1956 | Robinson . |
| 2,907,841 | 10/1959 | Campbell . |
| 3,279,249 | 10/1966 | Tocanne ............................... 324/664 |
| 3,421,077 | 1/1969 | Liu et al. ............................. 324/690 |
| 3,944,916 | 3/1976 | Tillander . |
| 4,026,467 | 5/1977 | Chevreliere . |
| 4,543,191 | 9/1985 | Stewart et al. ....................... 324/690 |
| 4,628,267 | 12/1986 | Lee et al. ............................. 324/690 |
| 4,652,811 | 3/1987 | Kwiat et al. . |
| 4,801,865 | 1/1989 | Miller et al. . |
| 4,885,529 | 12/1989 | Lee et al. ............................. 324/663 |
| 5,027,076 | 6/1991 | Horsley et al. ...................... 324/690 |
| 5,418,465 | 5/1995 | Seipler et al. ....................... 324/664 |
| 5,424,649 | 6/1995 | Gluck .................................. 324/690 |
| 5,479,104 | 12/1995 | Cambell .............................. 324/664 |

FOREIGN PATENT DOCUMENTS

| | | |
|---|---|---|
| 2101301 | 7/1972 | Germany . |
| 0172540 | 10/1983 | Japan ................................... 324/715 |
| 61-173145 | 1/1985 | Japan . |
| 4-262221 | 9/1992 | Japan .................................. 324/694 |
| 1824569 | 6/1993 | Russian Federation ............ 324/664 |
| 0322012 | 2/1979 | U.S.S.R. . |
| 0851245 | 6/1981 | U.S.S.R. .............................. 324/690 |

OTHER PUBLICATIONS

Cambridge University Press, Dec. 1976, "Applied Geophysics" by T. M. Telford et al, pp. 654–661.

*Primary Examiner*—Maura K. Regan
*Attorney, Agent, or Firm*—Francis A. Sirr; Earl C. Hancock; Holland & Hart llp

[57] ABSTRACT

A sensor for measuring moisture changes in soil and having an electrically insulating cylindrical body along which bare electrical conductors are placed. A transmitter produces constant alternating current which is supplied to the sensor. The voltage which this current creates in the soil is detected by the electrical conductors on the sensor and is fed to a receiver. The receiver consists of electronic circuitry for determining the necessity for allowing irrigation to occur, and if so, switches on a solenoid controlling the water supply. When the sensor indicates sufficient irrigation has occurred, the electronic controls switch the irrigation off. A tube sensor comprising rigid metal tubes of equal length and secured by end members such that no two tubes touch is also provided, for example to measure moisture content changes of any granular material. A plurality of the tube sensors are connected in series with insulated electrically conducting cables to form a string of tube sensors, thereby providing a means to obtain an average moisture content of large surface areas or volumes of material.

43 Claims, 11 Drawing Sheets

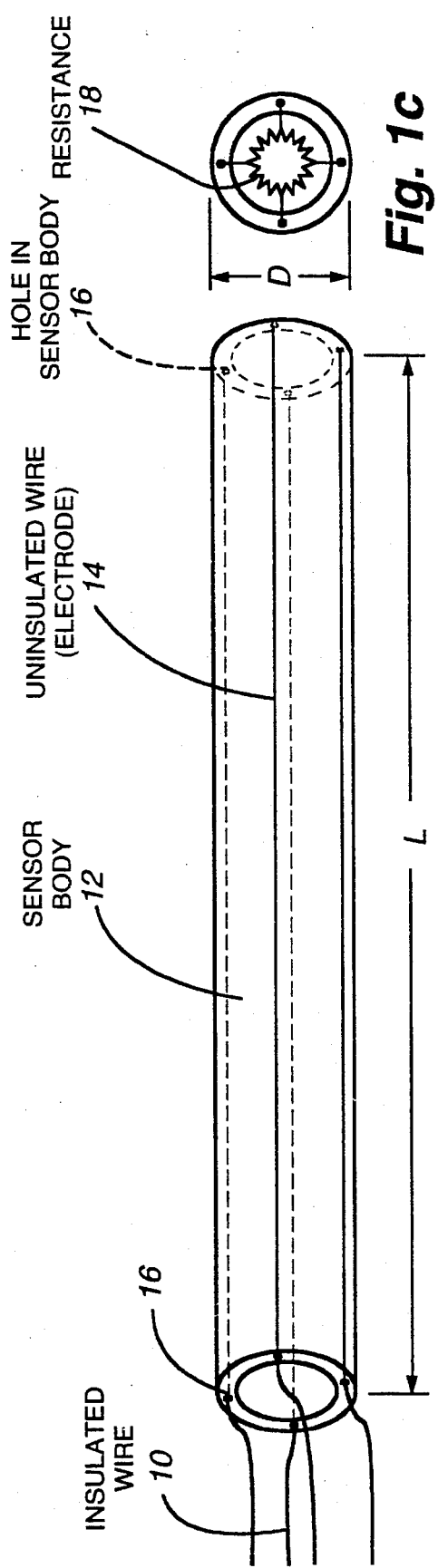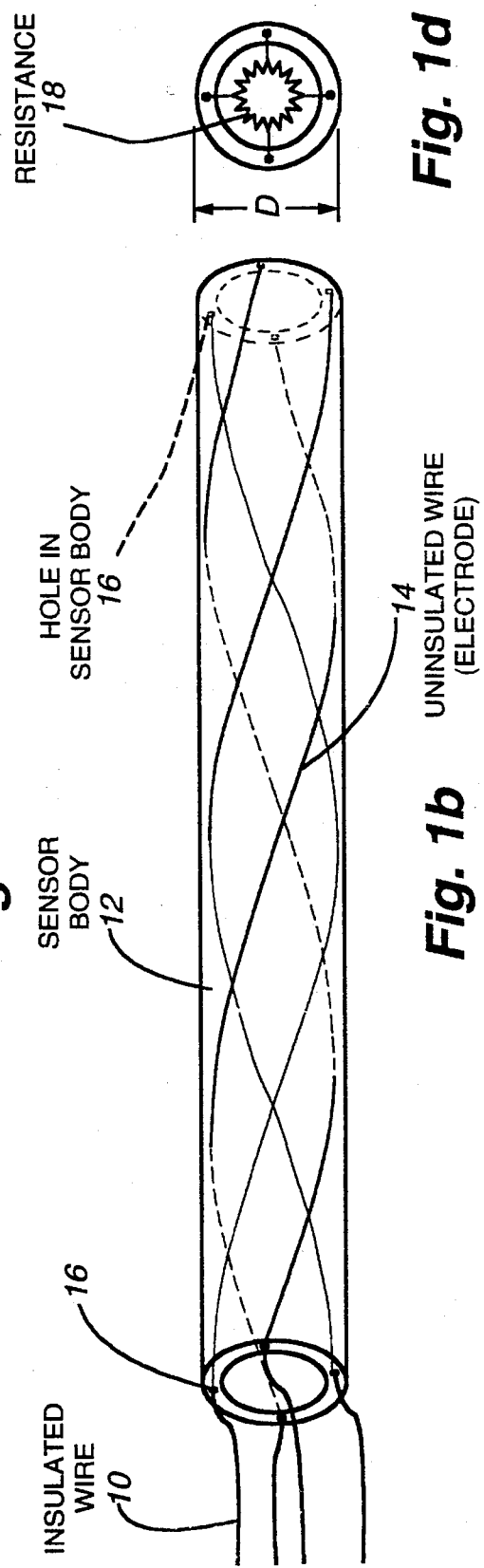

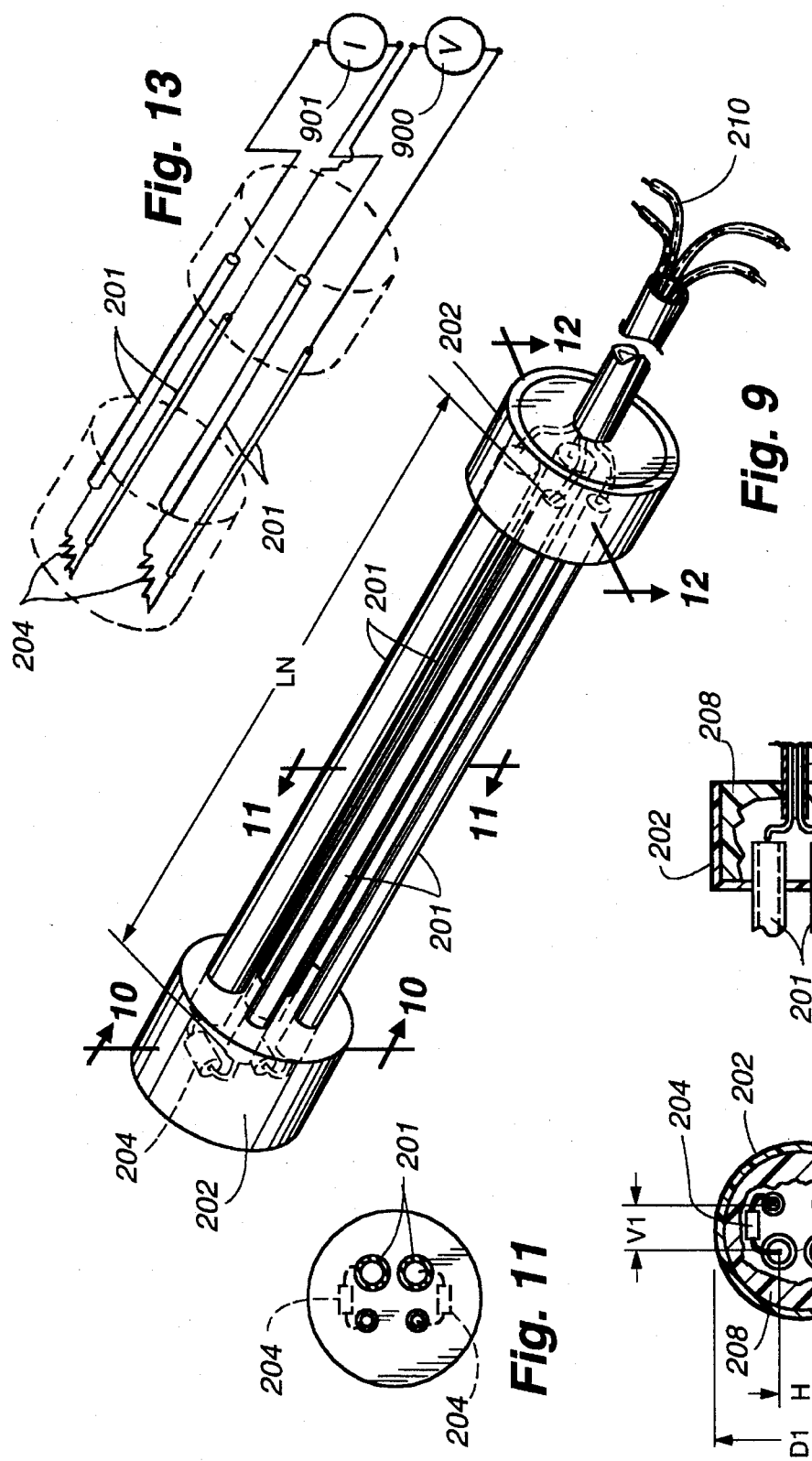

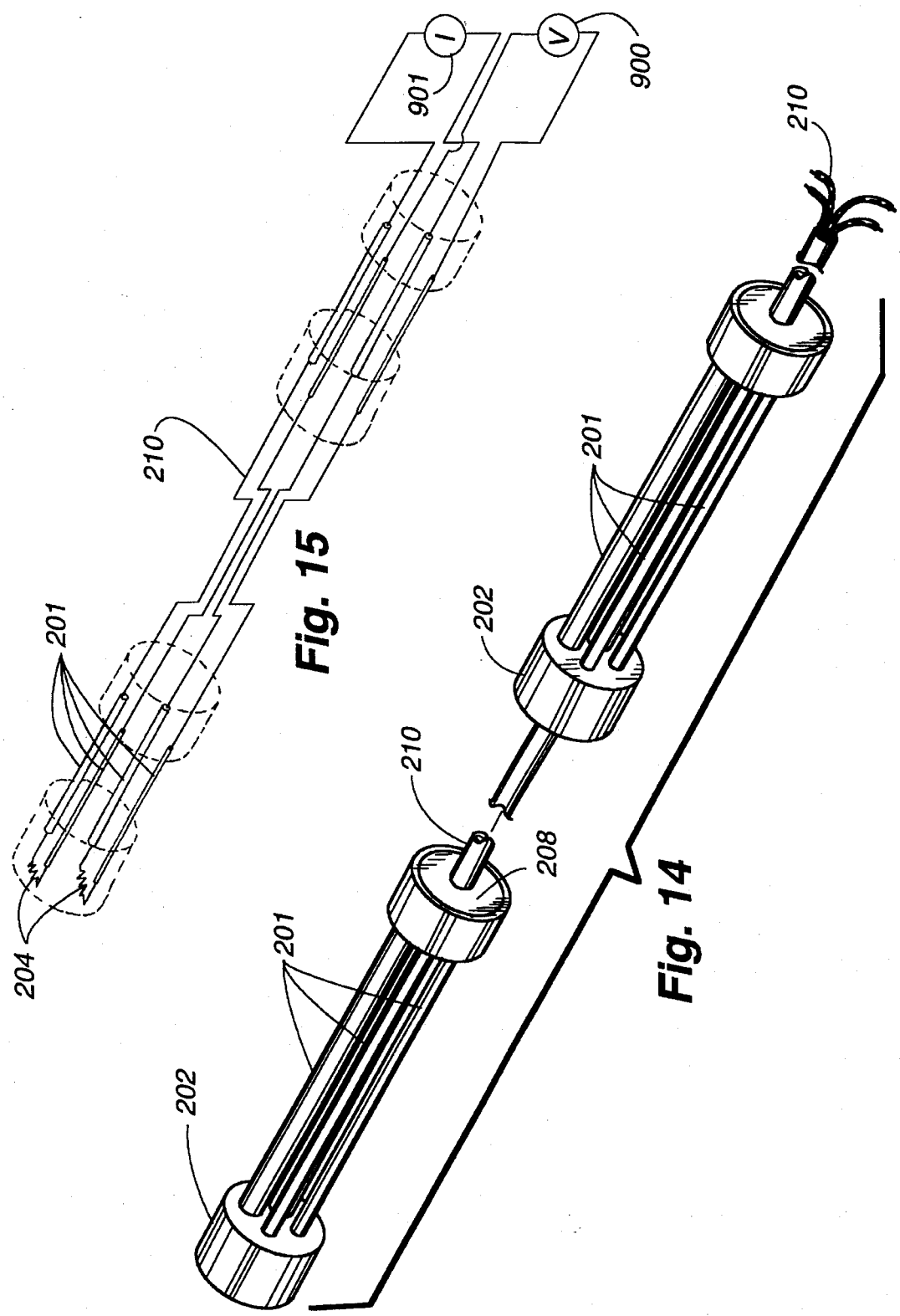

MOISTURE SENSOR AND CONTROL SYSTEM

This patent application is a continuation in part of copending patent application Ser. No. 08/057,871, filed May 7, 1993, and entitled "Moisture Sensor and Control System", now abandoned.

BACKGROUND OF THE INVENTION

1. Field of Invention

This invention relates to measurement of soil moisture, and to control of irrigation systems.

2. Description of the Related Art

Measurement of soil moisture is useful for minimizing the amount of irrigation water applied to growing plants, and for optimizing plant growth. Present uses of such systems are mostly confined to agricultural activities in dry climates where significant quantities of groundwater are required to maintain the crops. Minor use of such systems is made by homeowners, and some golf courses, wishing to conserve and optimize their use of water for grass. Soil moisture measurements are also used in groundwater studies. Soil moisture changes are also measured under and around waste sites, hazardous liquid lagoons and landfills in order to detect leaks.

The most common soil moisture sensor in use is a small gypsum block having a volume of about one cubic inch and encasing two metal electrodes. Gypsum absorbs moisture and the resistance across the two electrodes provides a measure of the moisture content within the gypsum. The gypsum blocks are buried in the soil at the depth where moisture content sensing is required, and the two wires from the electrodes are brought to the surface of the ground to facilitate resistance measurements. Gypsum blocks provide an indirect soil moisture indication since resistance measurement across the electrodes is influenced only by the moisture within the block. The block has to absorb moisture from the surrounding soil in order for this sensor to work. The degree to which this sensor will work depends on the packing density of the soil surrounding the block. Air space surrounding the block reduces its efficiency. Because gypsum has a strong affinity for water, the blocks tend to hold their absorbed water even when the surrounding ground is drying. This effect reduces sensitivity to soil moisture changes, in particular to drying soil, since the strong affinity for water exhibited by gypsum inhibits the block's capacity to lose water and hence indicate drying conditions. Since the gypsum must absorb water in order to detect increasing moisture content, and must dry out in order to detect reduced soil moisture, some time is required for these events to occur. This is especially true in the drying stage, and a considerable delay can occur between the time at which the soil has reached a certain level of dryness and the indication given by the gypsum block. With time, gypsum blocks disintegrate within the soil. The two electrode system used in these blocks essentially provides a measurement of the resistance of the electrode to gypsum contact along with the resistance of the gypsum. If the contact of either electrode with the surrounding gypsum changes, then a corresponding change in the resistance measurement, unrelated to soil moisture content, occurs.

Soil moisture is also measured using two electrodes placed in the ground. As with the electrodes in the gypsum block, this is a measurement of the resistance to ground, often called electrode resistance, of each of the electrodes, added to the resistance of the ground between the electrodes, which is usually fairly small compared to the electrode resistance since the current has a large volume of ground through which it can flow. Thus, the measurement of soil moisture using two electrodes is essentially a measurement of the electrode resistance. Any disturbance of the electrodes causes a change in the resistance measurement unrelated to the soil moisture content. U.S. Pat. No. 3,944,916 to Tillander (1976) proposes using two such electrodes to measure the resistance of soil in a plant pot. U.S. Pat. No. 4,026,467 to Chevreliere (1977) also uses two electrodes to measure the resistance of the region around the roots of a plant.

The measured resistance of two electrode systems also depends on the resistance of the wires used and changes when the length of the wires, and hence their resistance, is changed, or when any other resistance is included in the circuit. In addition, electrochemical effects result in voltages at the metal electrode to ground contact and must be accounted for.

An electrode system is proposed by Koller, West German Patent 2101301, (1972), where two electrodes are inserted into the soil to measure contact resistance. U.S. Pat. No. 2,768,028 to Robinson (1956) describes a sensor made of carbonaceous, electrical conducting material for measuring soil moisture. However, the patent does not describe the reason for the carbonaceous material nor the physics of the sensor.

Soil moisture is also measured using nuclear devices. These devices emit a stream of neutrons which interact with the hydrogen in the water molecules. Another technique which is now being used is called Time Domain Reflectometry which uses changes in the dielectric properties of soil to indicate moisture content changes. A similar method is called Frequency Domain Capacitance. However, these instruments are expensive and not appropriate for general irrigation purposes.

Some of the simpler, and less expensive devices include heat dissipation sensors and sensors containing fiber glass which work in essentially the same way as gypsum block sensors. Another method of measuring soil moisture is to use a Tensiometer. These devices have a porous medium and measure the suction strength created as the porous medium sucks water from the soil. As the soil dries, the suction becomes stronger. Comparison tests between a Tensiometer and the sensor described in this patent application show this sensor to be much more sensitive to moisture changes than the Tensiometer. Tests have also been conducted comparing Time Domain Reflectometry and gypsum blocks with this sensor, showing this sensor to be much more sensitive to moisture content changes that these other two methods.

The resistivity of the ground depends mostly on the soil moisture content and the salinity of the moisture, and can be measured using a four electrode array (Applied Geophysics, W. M. Telford, L. P. Geldart, R. E. Sheriff and D. A. Keys. *Cambridge University Press*, 1976; pages 654–661). With this system, in order to obtain good contact with the ground, the electrodes are one or two feet long. Two electrodes are used to pass electric current into the ground and the resulting voltage is measured across the other two electrodes. It is common with the four electrode systems to pass alternating current across the current electrodes, a procedure which removes the errors due to natural potentials at the electrode-soil contact along with naturally occurring noise, such as Telluric currents. An equation can be developed to calculate the resistivity of the ground involving the geometry of the electrode array, the amount of current injected into the ground and the resulting voltage. Often a linear array of equal spaced electrodes is used to measure resistivity. However, with this system, the resistivity measurement involves a volume of ground whose dimensions are related to the geometry of the electrode array. With the equal spaced electrode array, the volume of investigation is related to the electrode spacing, and a large volume of ground is sampled during measurements. Thus, very small electrode spacings are required to obtain resistivity values of small regions, such as around the root zones of grass. This means that small electrodes are required, thus increasing the problems of electrode contact with the soil and thus the injection of current into the ground. In addition, with the four electrode system, the lack of focusing of the electric currents allows these currents to flow in the more conductive regions of the soil. Thus, if shallow soil moisture is required for grass irrigation purposes and the ground a few inches below the root zone of the grass is wet, then the current will tend to flow in this wet ground, reducing the resistivity value measured and lowering the sensitivity of the resistivity measurement to the upper, and dryer, portions of the soil. A resistivity sensor is needed, therefore, where the volume of influence of the sensor is confined to the region of interest with good contact being made between the electrodes and ground while maintaining the advantages of the four electrode system.

If moisture measurements are attempted within a soil rich in clay, only very small changes are recorded during the time it takes grass to become water deficient. This is because most of the moisture is locked up in the fine pores of the clay and unavailable to the plant. If, however, moisture measurements are made in a small volume of sand placed at the root zone of the grass within this clay rich soil, then the moisture content of the sand changes dramatically, and provides a very sensitive indicator of the moisture requirements of the grass. The sensor described in this patent application can have its volume of influence reduced so as to be able to accurately record moisture changes in this small volume of sand.

Japanese Publication JA 61-173134 to Itagaki describes a moisture or temperature detecting element wherein a pair of electrodes are spirally formed on a ceramic circular body. A conductive material whose resistance changes with atmospheric gas occupies the space between the electrodes.

U.S. Pat. No. 2,907,841 to Campbell describes a bed wetting signal device wherein metal foil electrodes are placed in alternating fashion on a flexible polyethylene support for shorting by liquid or wet clothing. U.S. Pat. No. 4,801,865 to Miller et al describes a soil moisture probe wherein contact points are bridged by moisture. U.S. Pat. No. 2,636,962 to Bouyoucos describes a soil moisture meter that includes a variable resistance moisture absorption unit that is connected to be a portion of a resistance measuring bridge circuit. U.S. Pat. No. 4,652,811 to Kwiat et al describes a soil liquid content measuring device wherein spaced electrodes are placed in the soil, a voltage is applied to the electrodes, and the resulting electrode current flow is measured. Soviet Union document 0822012 by Badinter describes a humidity sensing device for use in a gas wherein uninsulated conductors are wound on a former that is coated with lithium chloride.

SUMMARY OF THE INVENTION

In summary, several objects and advantages of the invention are:

A) To sense changes in the amount of moisture in soil.

B) To respond to moisture changes in a soil volume that is very close to the sensor, or alternatively, to include moisture changes some distance away from the sensor. Thus, the volume of influence of the sensor can be changed. The sensor is designed such that it can respond to a well defined region at the root zone of grass.

C) To provide a soil moisture change sensor that is not influenced by electrochemical voltages at the electrode to ground contact.

D) To provide a soil moisture change sensor which is not influenced by the resistance or length of the wires that connect to the sensor.

E) To provide a soil moisture change sensor which uses the increasing resistance to ground of the electrodes as the soil dries to enhance the measured response.

F) To respond virtually instantaneously to soil moisture changes.

G) To be easy and inexpensive to build.

H) To be durable under all soil conditions.

I) To provide electronic circuits to allow easy installation and use of the sensor for monitoring and controlling the irrigation of lawns or other irrigation requirements.

J) To provide electronic circuits such that water saturated ground conditions can be memorized by the instrument along with the dry condition of the ground indicating irrigation is needed and to provide a means whereby these settings can be easily changed.

K) To provide a visual means whereby the current state of soil moisture can be observed at any time.

L) To provide electronic controls so that irrigation is allowed only when soil moisture is sufficiently low. Also to provide electronic controls to shut off irrigation when the sensor indicates sufficient irrigation has occurred, and to allow an operator controllable delay time to take effect after the sensor indicates sufficient irrigation has occurred, thereby allowing watering to continue for the delay time.

M) To provide measurements, which when made over a long time interval, will indicate increases in salt content of the soil.

Further objects and advantages of this invention will become apparent from a consideration of the drawings and the ensuing description.

BRIEF DESCRIPTION OF THE DRAWING

FIGS. 1a–1d show the sensor of this invention with two different wire electrode arrangements.

FIG. 9 shows the construction of a four-tube tube sensor in accordance with the invention.

FIG. 10 shows a cross section through the left hand end member of the tube sensor of FIG. 9 that contains two resistors.

FIG. 11 shows a cross section through the central part of the tube sensor of FIG. 9.

FIG. 12 shows a cross section through the right hand end member of the tube sensor of FIG. 9 that contains the four wires that are connected one wire to each of the four tubes of the tube sensor.

FIG. 13 shows the arrangement of the two electrical resistors and the current transmitter and voltage receiver that are connected to the four wires of the tube sensor of FIG. 9.

FIG. 14 shows two tube sensors of FIG. 9 serially joined to form a string sensor.

FIG. 15 shows the arrangement of the two electrical resistors, the four wires, the current transmitter, and the voltage receiver that are connected to the string sensor of FIG. 14.

Reference Numerals In Drawings

Figure 2:
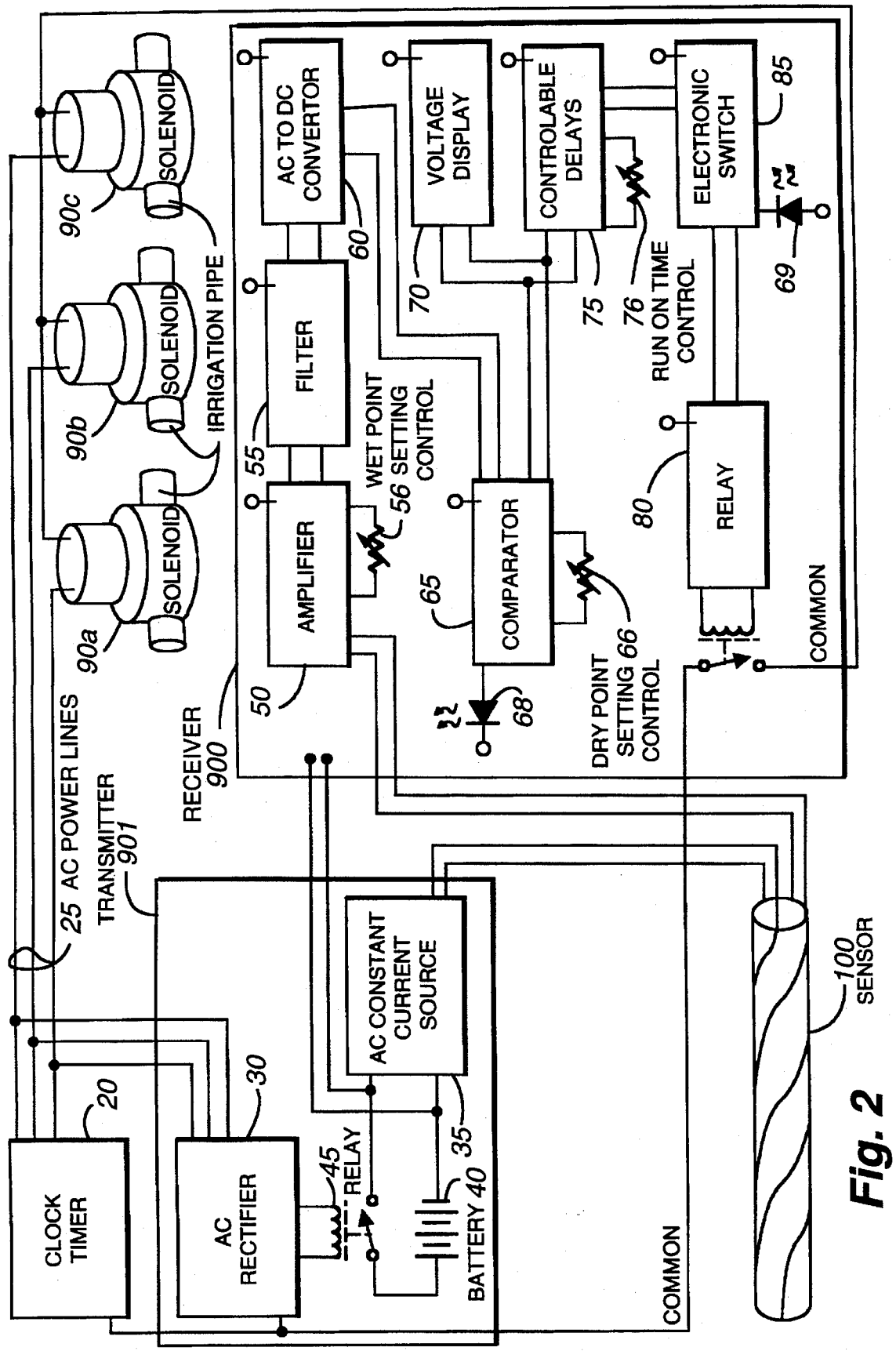
FIG. 2 shows a block drawing of the electronics and the sensor when one sensor is used for three solenoids.

10 Insulated electrical conductor (Wire)
12 Sensor body
14 Uninsulated wire (Electrode)
16 Hole in sensor body
18 Electrical Resistance
L length of sensor
D Diameter of sensor
T Number of complete turns each wire electrode makes around sensor body
20 Clock timer
25 Alternating Current (AC) Power lines from clock timer
30 AC rectifier
31 Electrically controlled switches
35 AC Constant Current Source for sensor
36 Constant Current Diode, number LM334
37 Switch. Allows different current magnitudes to be selected.
40 Battery. Power supply for sensor current and electronics.
45 Relay. Switches battery power on when AC power is switched on.
50 Amplifier
55 Filter
56 Wet Point Setting Control
60 AC to DC convertor
61 Integrated circuit; CD4066
62 Integrated Circuit; CD4047
65 Comparator
66 Dry Point Setting Control
68 Light emitting diode to show state of output from comparator 65
69 Light emitting diode to show when relay 80 is closed
70 Voltage Display
75 Controllable delays. Allows delays to be set on startup and shutdown of the system.
76 Run On Time Control. Allows watering to continue after sensor indicates irrigation is sufficient.
80 Relay. Switches continuity of common line and activates solenoid.
82 Oscillator. Provides clock input to Electronic Switch 85.
85 Electronic Switch. Controls relay 80 switching.
86 Transmitter grounding point for a two and three wire system.
87 Receiver grounding point for a two wire system.
90a, 90b, 90c Solenoids for allowing irrigation water to flow.
100a, 100b, 100c Sensors
900 Receiver
901 Transmitter
201 Metal tube (electrode)
202 End member
204 Electrical resistance
206 Hole in end member
208 Electrically insulating filler
210 Electrically insulated wire
LN Length of metal tube (electrode)
H Distance between larger diameter metal tubes (electrodes)
V1 Distance between the first larger diameter metal tube (electrode) and an adjacent smaller diameter metal tube (electrode)
V2 Distance between the second larger diameter metal tube (electrode) and an adjacent small diameter metal tube (electrode)
DI Outside diameter of the end member of a tube sensor

DETAILED DESCRIPTION OF THE INVENTION

FIG. 1. Sensor Design

A typical embodiment of a sensor in accordance with the invention is illustrated in FIGS. 1a and 1b. Sensor body 12 is made from any electrically insulating material, is cylindrically shaped, and has four small holes 16 drilled into each end of sensor body 12. Holes 16 are equally spaced round the circumference of sensor body 12. An uninsulated wire 14 is threaded through one of the holes 16 and then travels along the outer surface of sensor body 12 to another hole 16 at the other end of sensor body 12 where the wire is secured. Three additional wires are positioned, as just described, in the three remaining holes 16 at each end of sensor body 12. Electrical resistances 18 are then soldered between each of the wires or electrodes 14 at the right hand end of sensor body 12.

In one embodiment (FIG. 1a), wires 14 travel in a straight line along the surface of sensor body 12 to the other end of sensor body 12, where the wires are threaded through holes 16 and secured. In another embodiment (FIG. 1b), the wires 14 travel one complete revolution round the circumference of sensor body 12. The number of complete revolutions traveled around sensor body 12 by the wires is designated T. In addition to the four wire sensors of FIGS. 1a and 1b, a two or a three wire sensor can be used.

FIG. 2. Electronic Circuit, One Sensor

FIG. 2 shows one embodiment of the complete system for measuring soil moisture and for controlling irrigation. The main electronic parts are defined as a transmitter 901 and a receiver 900. The other components are sensor 100, existing clock timer 20, and the existing solenoids 90a, 90b and 90c.

Transmitter 901 comprises AC rectifier 30, relay 45, battery 40 and AC constant current source 35. Receiver 900 consists of amplifier 50, filter 55, AC to DC convertor 60, comparator 65, voltage display 70 consisting of a display driver and 10 light emitting diodes (LED's), an integrated circuit for producing controllable delays 75, electronic switch 85, relay 80, three variable resistors 56, 66 and 76 and two light emitting diodes 68, 69.

Existing clock timer 20 is shown with three AC power wires 25 connected to three solenoids 90a, 90b and 90c for controlling irrigation, and a common wire connected to AC rectifier 30, relay 80 and the three solenoids 90a, 90b and 90c. A connection is made to each of the three AC power wires 25 and fed into AC rectifier 30. Relay 45 is connected to AC rectifier 30. The switched side of relay 45 is connected to battery 40. The output from battery 40 is connected to AC constant current source 35 and to receiver 900. The output from AC constant current source 35 is connected to sensor 100. Two wires from sensor 100 are connected to amplifier 50 in receiver 900. A variable resistance 56, allowing the wet point setting to be made, is connected to amplifier 50. The output from amplifier 50 goes into filter 55 and then to AC to DC convertor 60. The output from 60 goes to comparator 65. Variable resistance 66 is connected to comparator 65 allowing the dry point setting to be made. A light emitting diode 68 is connected to the output from comparator 65. The output from comparator 65 goes to voltage display driver 70 and to controllable delays 75. Variable resistance 76 is connected to controllable delays 75 allowing the run on time 76 to be set. The output from controllable delays 75 is connected to electronic switch 85. A light emitting diode 69 is connected to electronic switch 85. The output from electronic switch 85 is connected to relay 80. The switching side of relay 80 is connected to the common wire. One side of this common wire comes from clock timer 20 and the other side of the common wire goes to solenoids 90a, 90b and 90c.

Figure 3A:
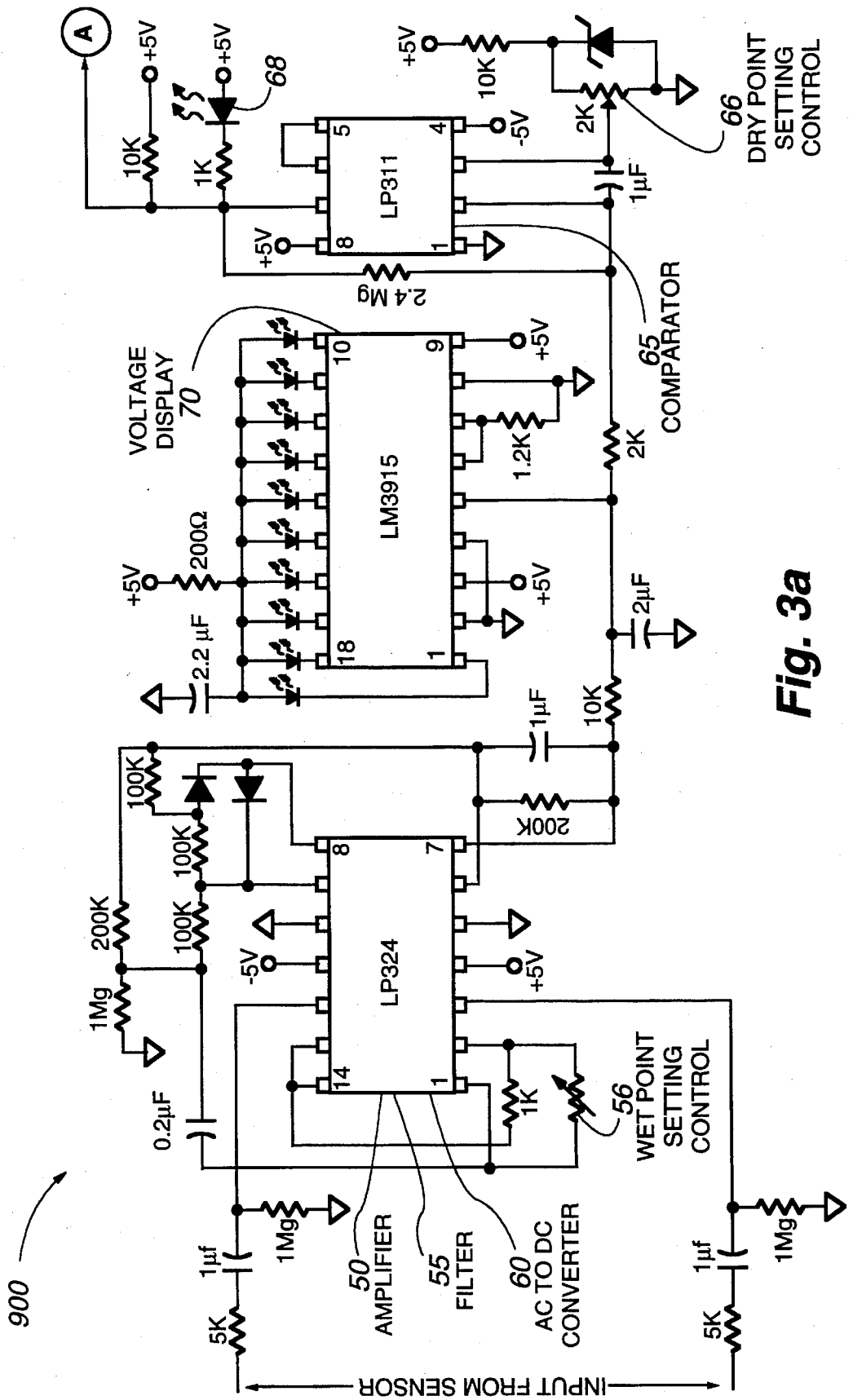
FIG. 3 shows the electronic components and wiring for the receiver electronics of FIG. 2.
Figure 3B:
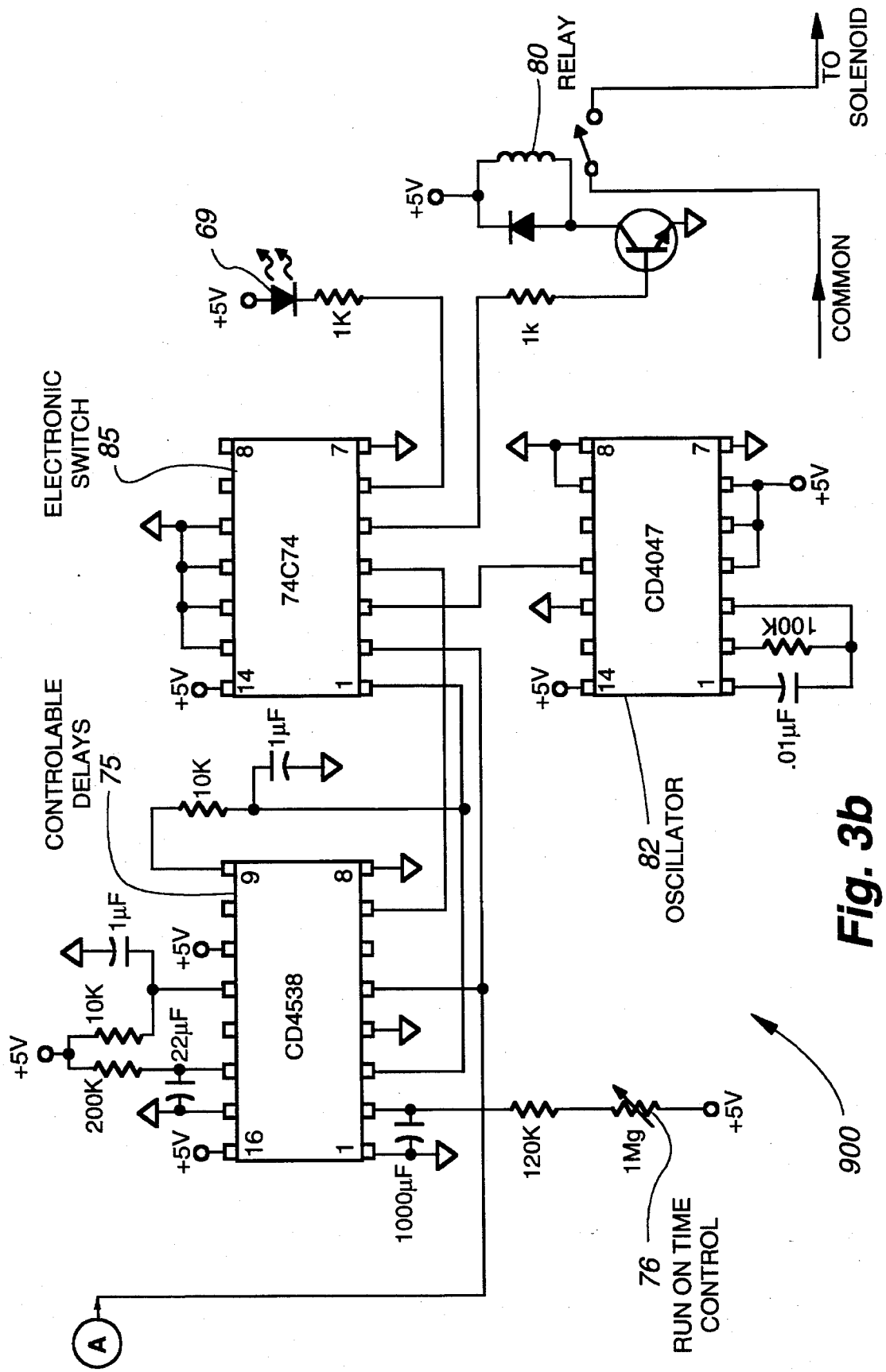

FIG. 3. Receiver Electronics

FIG. 3 shows one embodiment of the electronic circuits used to measure the signals from a single sensor 100, and to then control the irrigation timing according to the moisture requirements.

Wires from sensor 100 are connected to amplifier 50 in Receiver 900. Variable resistance 56 connected to the amplifier 50 is used to set the wet point setting. The output from amplifier 50 connected to a 0.2 microfarad capacitor and then to AC to DC convertor 60 comprising three 100 ohm resistors, one 201 ohm resistor, one operational amplifier and two diodes. Output from AC to DC convertor 60 is filtered and connected to voltage display driver 70. Voltage display driver 70 is then connected to comparator 65. Output from comparator 65 is connected to controllable delays 75. A light emitting diode 68 also connected to the output from comparator 65. Various resistors and capacitors, illustrated on FIG. 3, are connected to controllable delays 75 in order to set the delays. Controllable delays 75 are then connected to electronic switch 85. Integrated Circuit (IC) CD4047 is used as an oscillator 82 and is connected to electronic switch 85 in order to provide a clock mechanism to drive 85. Output from electronic switch 85 is connected to relay 80. Another output from 85 is connected to a light emitting diode 69.

Figure 4:
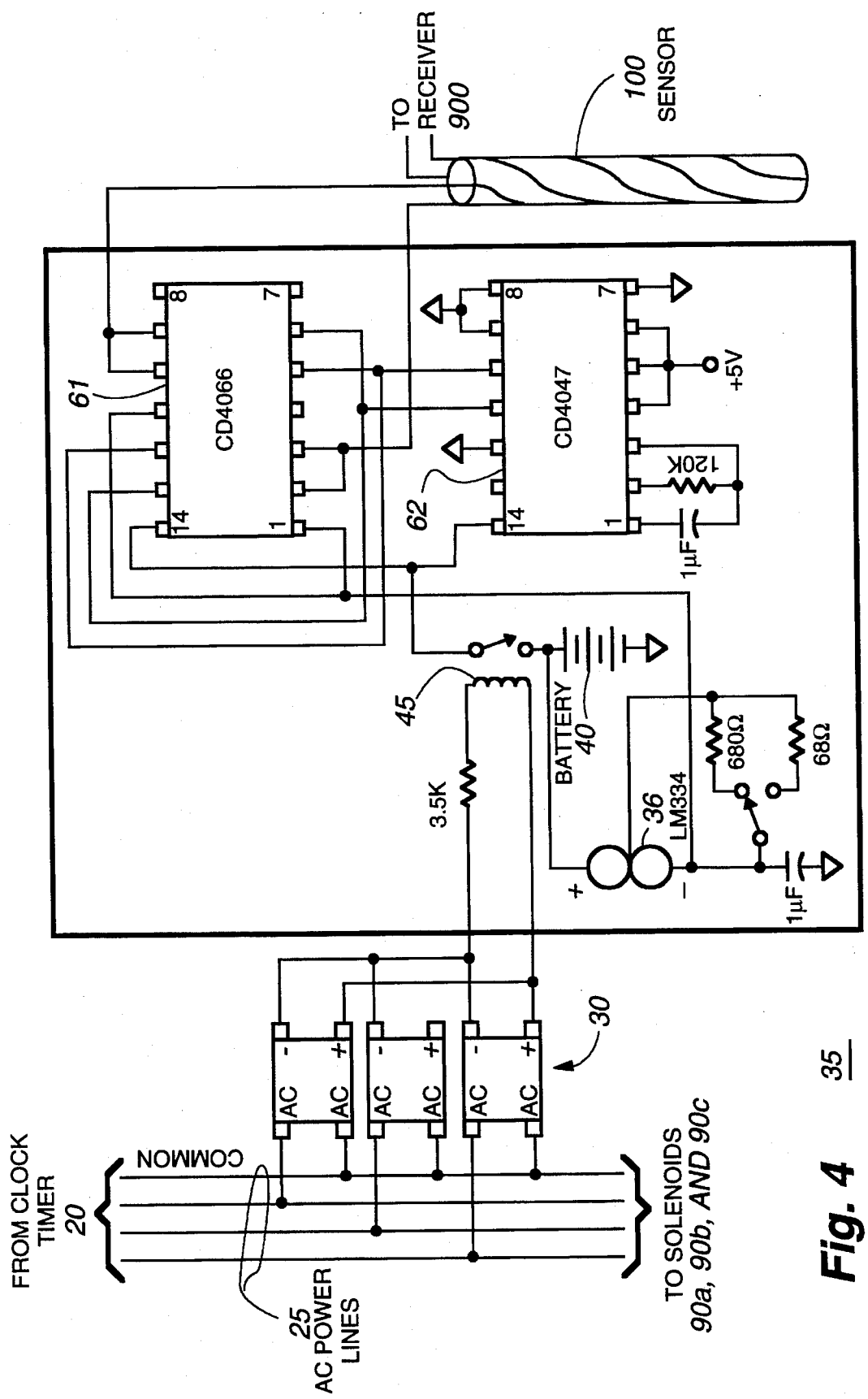
FIG. 4 shows the electronic components and wiring for the AC Constant Current Source of FIG. 2.

FIG. 4. AC Constant Current Source: Transmitter

FIG. 4 shows one embodiment of the AC constant current source 35 used to provide current to the sensor.

Three AC power lines 25 connect clock timer 20 to solenoids 90a, 90b and 90c (FIG. 2). Connections are made from each of these three AC power lines 25 to three AC rectifiers 30. The output from rectifiers 30 are connected to relay 45. The switched side of relay 45 is connected to battery 40 and to a current limiting diode 36. The switched side of relay 45 is also connected to two integrated circuits CD4047 62 and CD4066 61 as shown in FIG. 4. A resistor and capacitor are connected to 62 as shown in FIG. 4. Integrated Circuit CD4066 61 is connected to sensor 100.

Figure 5:
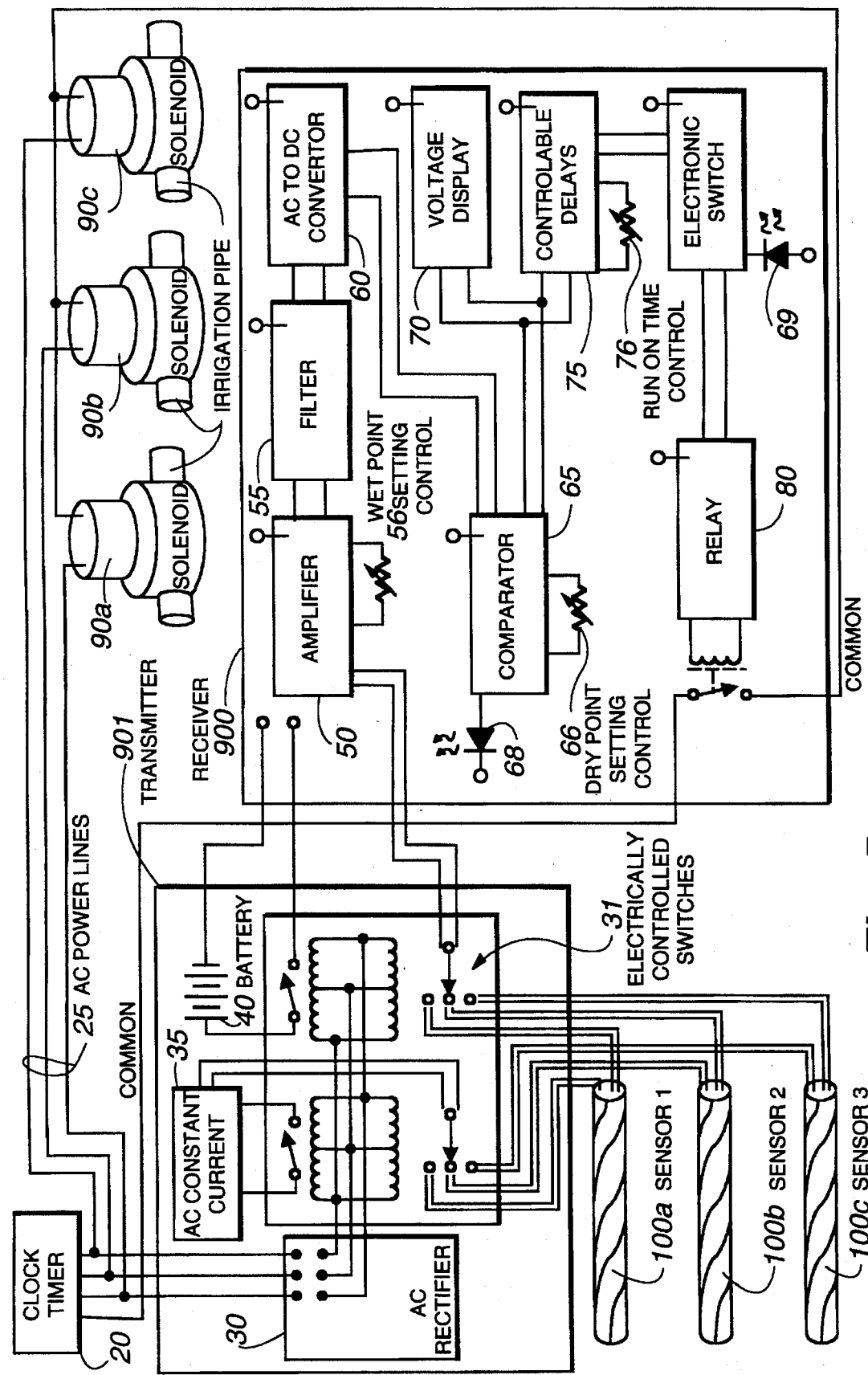
FIG. 5 shows a block diagram of the electronics and sensors when three sensors are used, each controlling the receiver electronics independently.

FIG. 5. Electronic Circuit, Multiple Sensors

FIG. 5 shows one embodiment of the electronic circuits used to measure the signals from three sensors 100a, 100b and 100c and to then control the irrigation timing using the three sensors each of which controls relay 80 independently.

Clock timer 20 is shown with three AC power wires 25 connected to three solenoids 90a, 90b and 90c for controlling irrigation, and a common wire. A connection is made to each of the three AC power wires 25 and fed into AC rectifier 30. The output from AC rectifier 30 is connected to four electrically controlled switches. These switches are connected to sensors 100a, 100b and 100c, battery 40 and amplifier 50. Receiver 900 is identical to that used when only one sensor 100 is used and is described earlier under the heading FIG. 2, Electronic Circuit, one sensor.

Figure 6:
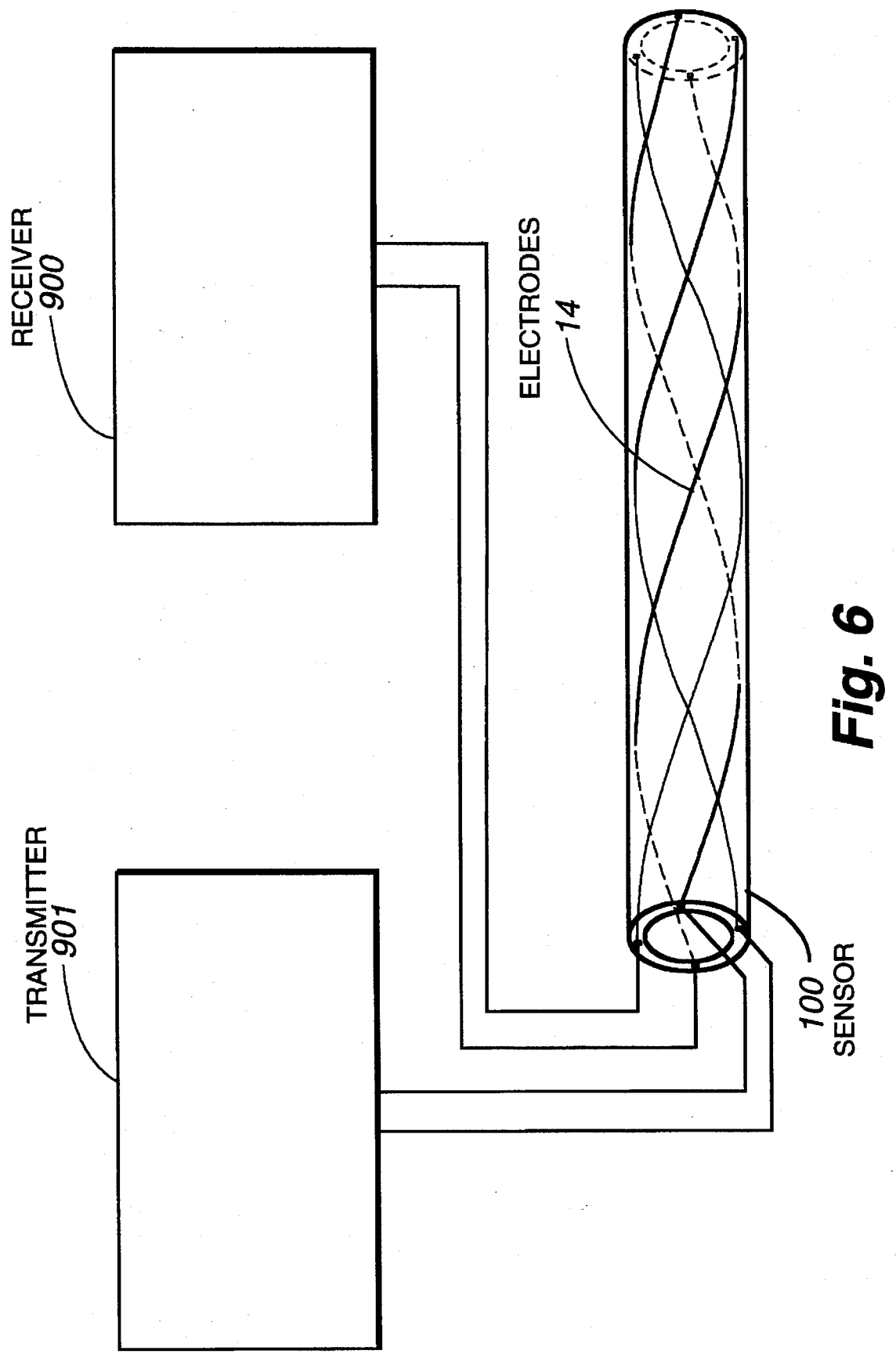
FIG. 6 shows the wire arrangement used with a four electrode system.

FIG. 6. Four Wire System

FIG. 6 shows sensor 100 with four electrodes 14. Two wires connect Transmitter 901 to sensor 100. Two different wires from sensor 100 are connected to receiver 900.

Figure 7:
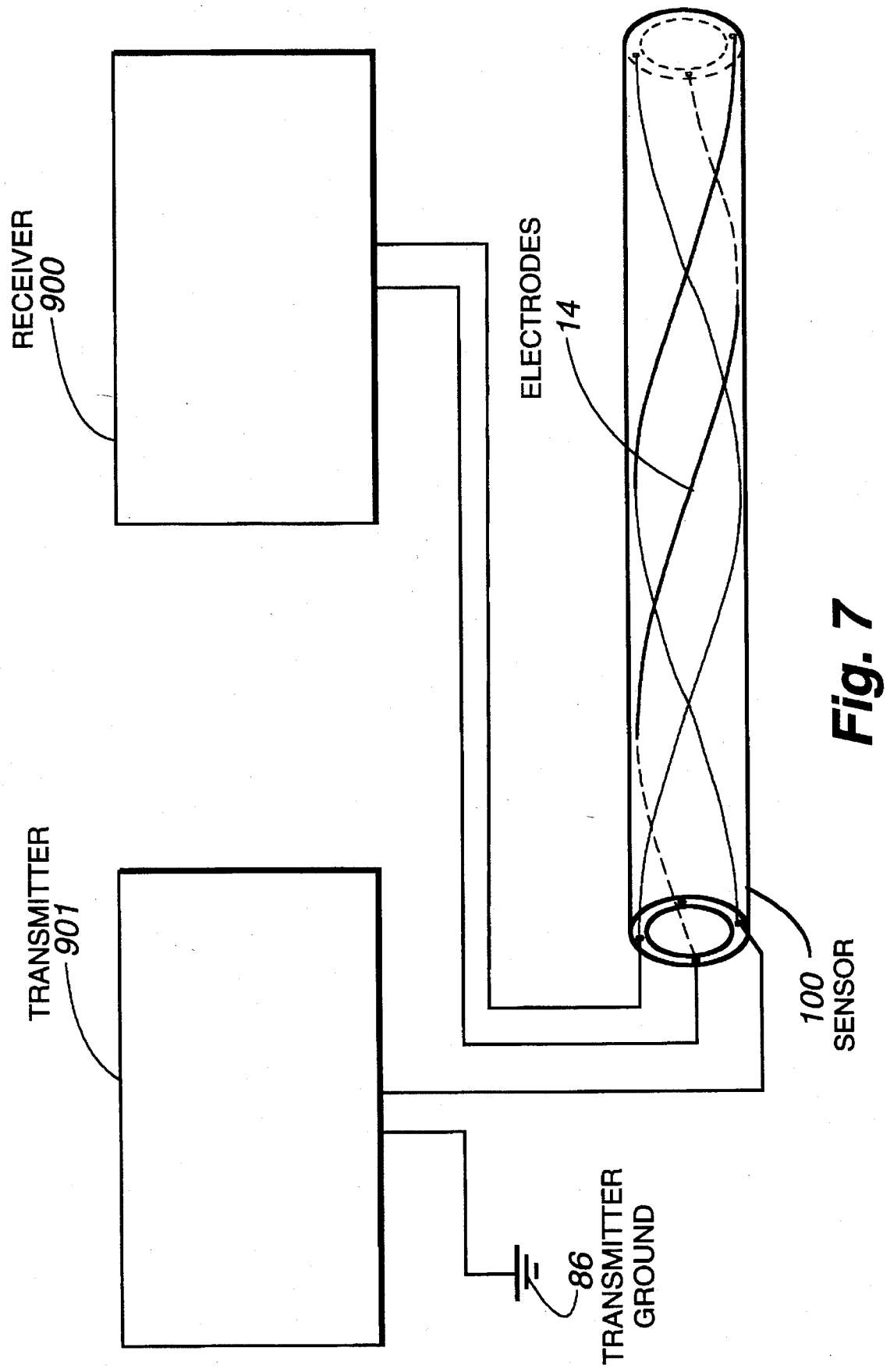
FIG. 7 shows the wire arrangement used with a three electrode system.

FIG. 7. Three Wire System

FIG. 7 shows a sensor with three electrodes 14. One wire from transmitter 901 is connected to sensor 100. Another wire from transmitter 901 is connected to ground 86. Two wires from sensor 100 are connected to receiver 900.

Figure 8:
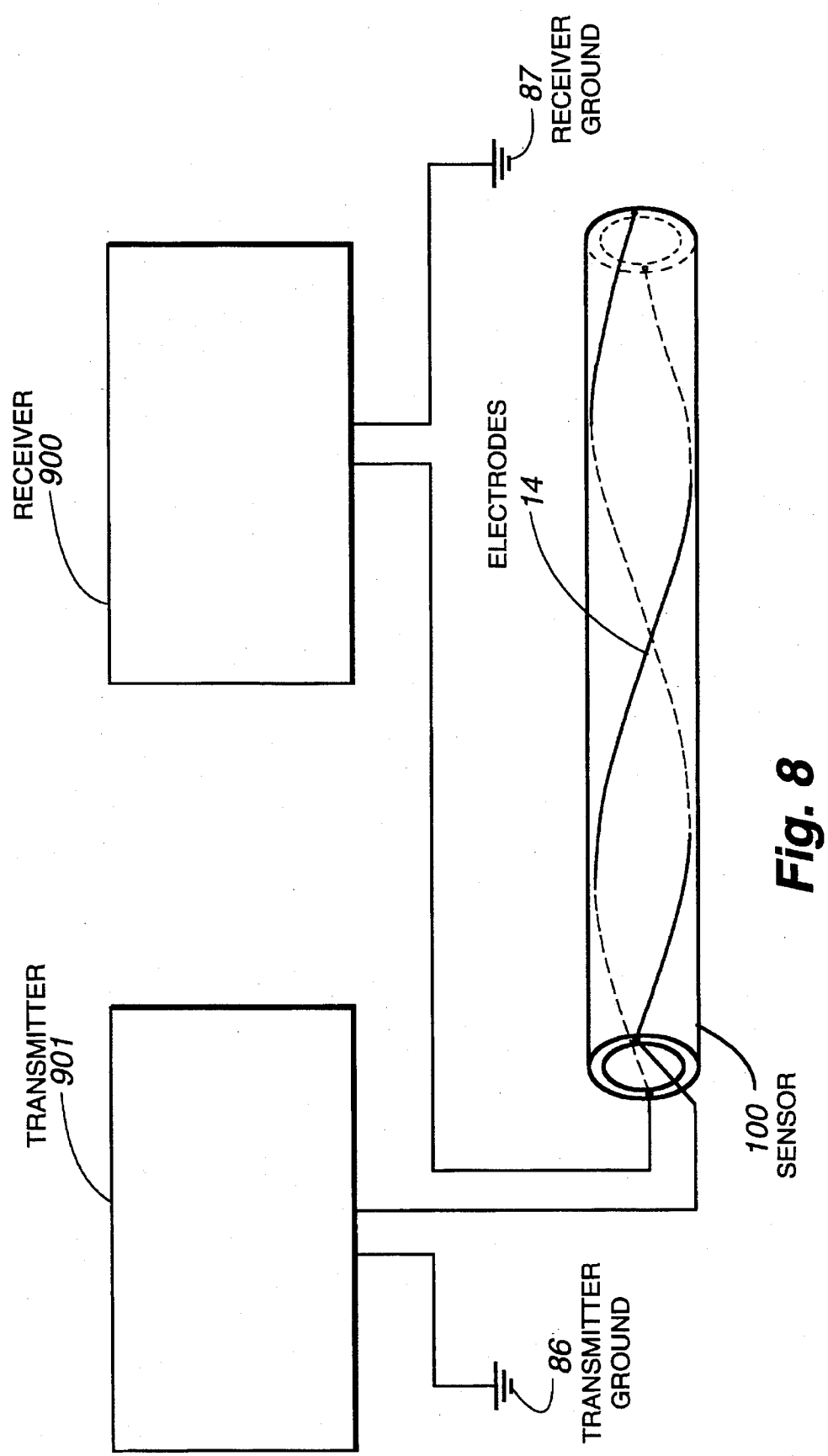
FIG. 8 shows the wire arrangement used with a two electrode system.

FIG. 8. Two Wire System

FIG. 8 shows a sensor with two electrodes 14. One wire from transmitter 901 is connected to sensor 100. One further wire from transmitter 901 is connected to ground 86. A different wire from sensor 100 is connected to receiver 900. Another wire from receiver 900 is connected to ground 87.

FIGS. 9, 10, 11, 12, 13, 14 and 15. Tube Sensor

FIG. 9 shows a typical embodiment of a sensor whose construction is different from the sensor shown on FIG. 1. The sensor of FIG. 9 is called a tube sensor. Either solid metal bars or hollow metal tubes 201 are used as electrodes. Metal tubes 201 are preferable straight and parallel tubes, and can be made from any metal which conducts electricity and maintains structural rigidity. If long life is required, the metal could be covered with a thin film of gold to stop all electrochemical corrosive effects. A typical embodiment of a tube sensor has brass metal tubes 201.

The left hand ends of the four metal tubes 201 are inserted into holes 206, as illustrated in FIG. 10, that are drilled into an rigid nonconductive plastic end member 202, and these ends are secured thereto by the use of conventional and noncritical attachment means. The right hand ends of the four metal tubes 201 are also fitted into four similarly spaced holes 206 in a second similarly shaped end member, and are then secured thereto. In a typical embodiment of a tube sensor the tube securing mechanism is an electrically resistive, and preferably nonconductive, resin 208, as illustrated in FIG. 12, which is poured into the hollow end member 202.

In a typical embodiment of the invention, the tube sensor or sensors of FIGS. 9–15 have current electrodes 201 that are of a larger diameter than the diameter of the voltage electrodes 210. This construction and arrangement decreases the electrical resistance between the current electrodes and the surrounding medium, such as soil. However, within the spirit and scope of the present invention a tube sensor(s) can be provided having current and voltage electrodes that are of the same diameter.

At the left hand end of the tube sensor, one end of an electrical resistance 204, shown in FIG. 11, is soldered onto the left hand end of one of the large-diameter metal tubes 201, and the other end of this same electrical resistance 204 is soldered onto the left hand end of a small-diameter metal tube 201. The end of a second electrical resistance 204 is soldered onto one end of a second large-diameter metal tube 201, and the other end of this electrical resistance 204 is soldered onto the end of a second small-diameter metal tube 201. In a typical embodiment of a tube sensor, the above-mentioned second electrical resistance 204 is placed on the same end of the tube sensor as the above-mentioned first electrical resistance 204. For each pair of metal tubes 201 that are joined together by an electrical resistance 204, one of the metal tubes 201 is designated a current electrode and the other metal tube 201 is designated a voltage electrode. Thus, the typical tube sensor shown in FIG. 13 has two large-diameter metal tube current electrodes 201 which are connected to two small-diameter metal tube voltage electrodes 201 by two resistors.

Typical dimensions for the tube sensor of FIG. 9 are a length LN of about 10 cm and a diameter DI of about 2.5 cm. Typical diameters of the metal tube electrodes 201 are about 3 mm. Typical values for the resistances 204 are about 1 Meg-ohm. Typical values for H, V1 and V2 are all equal to about 1 cm. Electrically insulating filler 208 is an electrically resistive resin in a typical embodiment of a tube sensor. This resin, which is initially a liquid, sets and secures the portions of the metal tubes 201 which protrude into the end member 202. The resin also protects the electrical resistors 204 and the electrically insulated wire 210 that connects to metal tube electrode 201 from moisture.

FIG. 13 illustrates the wire connections from a current transmitter 901 and a voltage receiver 900 to a typical embodiment of a tube sensor in accordance with the invention. This figure also illustrates a typical arrangement of resistances 204 connected to metal tube electrodes 201. Current transmitter 901 is designated I. Voltage receiver is designated V. In the typical embodiment of a tube sensor, current transmitter 901 is connected to two adjacent large-diameter metal tube electrodes 201 with individual electrical resistors 204 for each electrode, as illustrated on FIG. 13. Voltage receiver 900 is connected to the remaining two small-diameter adjacent metal tube electrodes 201.

Electrical resistors 204 allow the voltage that is measured across the small-diameter voltage electrodes 201 to be greatest in very dry conditions, when very little current flows from large-diameter current electrodes 201 into the surrounding soil or ground. Resistances 204 could be removed if the amount of electrical current entering the ground was measured. In order to obtain a voltage measurement which then indicates moisture changes in the ground, the measured voltage across the voltage measuring electrodes 201, measured by receiver 900, is divided by the amount of current entering the ground. The amount of current entering the ground is measured using a resister (not shown) that is placed in series between current transmitter 901 and one of the two current electrodes 201. This series resistor is called a current sense resistor. As more current flows through this series resistor, a greater voltage drop exist across this resistor and this voltage drop in measured. Electronic circuits then divide the measured voltage across the two voltage electrodes 201 by the voltage across the current sense resistor.

FIGS. 14 and 15 illustrate two tube sensors joined together in series in order to form a string sensor. String sensors are designed to provide a better measure of the relative moisture content of large areas or volumes of soil. A typical string sensor contains three tube sensors that are joined by 5 meters of wire. However, much longer lengths of wire could be used if required. The only restriction on the length of wire to be used is that the electrical resistance of the wire be-kept to a reasonable value. It is expected that a reasonable value would be anything less than a few hundred ohms.

FIG. 15 illustrates the connections between current transmitter 901 and two of the metal tube electrodes 201. FIG. 15 also illustrates the wire connections between the voltage receiver 900 and the other two metal tube electrodes 210. This figure also shows resistances 204 that are connected between the electrodes. In string sensors, resistances 204 are typically placed only on the last tube sensor of the sensor string; i.e., the left hand tube sensor in FIG. 15. Resistances 204 can theoretically be placed anywhere on the tube sensors, or on the wires leading to the sensors. In a typical embodiment of a tube sensor, resistances 204 are placed at the end of the sensor opposite to the wire connection to the current transmitter and voltage receiver, as shown in FIG. 15. In a typical embodiment of a string sensor, resistances 204 are placed at the end of the last tube sensor in the string; i.e., at the furthest point from the voltage receiver and current transmitter.

The two current electrode metal tubes 201 are required to transmit electrical current into the surrounding soil. The greater the electrode surface area that is in physical contact with the soil, the better will be the transference of electrical current into the soil. Thus, the diameter of the two metal tubes 201 being used as current electrodes can be increased to increase their surface area. In addition, the length of the two current electrode metal tubes 201 can be increased in order to increase the surface area of the metal tube 201. Metal tube electrodes 201 for current transmission can have diameters from about 2.5 mm to about 6 mm. Larger, or smaller, values could be used if required.

In a typical tube sensor, the metal tube electrodes 201 have values of H, V1 and V2 which are equal. Thus, the cross section are formed by the four metal tube electrodes 201 forms a square. These quantities are illustrated in FIG. 10. In other embodiments of a tube sensor in accordance with the invention, the value of V1 and V2 are made smaller than the value of H. This allows the magnitude of the measured voltage to be modified. Further measured voltage modifications can be provided by making V1 and V2 different.

Operation FIGS. 1a, 1b, 2, 3, 4, 5, 6, 7, 8, 9, 13, 14 and 15

FIGS. 1a and 1b, Sensor Design

The operation of the sensors requires that the associated electronics also be described. This is done within this section under the heading FIG. 2, Electronic Circuit, one sensor. The following section describes the attributes of the sensors and how these attributes can be changed.

The parameters which can be set during assembly are the length of the sensor L, its diameter D, and the number of complete turns around sensor 100 that each wire electrode makes, T. Sensor 100 responds to changes in moisture content of the soil that is local to sensor 100. In a typical sensor 100, an alternating electrical current having a constant magnitude is passed through two adjacent electrodes 14 called current electrodes. Simultaneously, the voltage induced by this current is measured across the other two electrodes 14 called the voltage electrodes. The degree to which the ground conducts electricity is largely dependent on the amount of moisture it contains and the conductivity of this moisture which depends on its salinity. If the medium (soil) surrounding sensor 100 is dry, then a large voltage will be observed across the voltage electrodes when current is passed through the current electrodes. Conversely, when the ground is wet, only a small voltage is observed across the voltage electrodes. Generally, sensor 100 is influenced by a cylinder of soil whose axis coincides with that of sensor 100. The dimensions of this cylinder can be changed by altering the values of D, L and T during the assembly of sensor 100. The number of electrodes 14 is considered an operational characteristic and is discussed later. The diameter of sensor 100, D, influences the radius of influence of sensor 100. A large diameter has a larger radius of influence. The value of T also influences the radius of investigation of sensor 100. In addition, a larger value of T provides a greater length of electrode and hence a greater area of the electrode in contact with the surrounding soil, thereby improving electrical contact with the soil. A larger value of T reduces the radius of investigation of sensor 100. When T is 1 the radius of influence of sensor 100 is two or three times the radius of sensor 100. The length of sensor 100, L, influences the length of the soil's cylinder of influence of sensor 100. A large value of L also increases the area of electrode in contact with the soil, thereby increasing the ease with which current can be transmitted from sensor 100 into the soil. Correct design and placement of sensor 100 is important for proper operation. If irrigation requirements are to be assessed at the root zone of grass, then a sensor 100 with a small radius of investigation is required. If a sensor 100 is required to monitor the moisture content of the roots of a tree, then a larger radius of investigation is required. Resistors 18 ensure that, in very dry conditions when no current flows from the electrodes into the ground and hence no ground voltage is generated to be measured, then the highest voltage possible is measured, thereby correctly indicating very dry conditions. Resistance 18 between the current electrodes and the voltage electrodes can be changed to further increase the measured voltage under dry conditions. These resistances feed voltage from the current electrodes to the voltage electrodes. A constant current is provided by constant current diode 36. When the ground is dry, diode 36 produces a greater voltage so as to drive current into the ground. Resistances can be chosen such that this increase in voltage can be sensed by the voltage electrodes and is added to the voltage provided from current flowing into the ground. The resistances used are chosen such that this effect is only measurable under very dry conditions, since sensor 100 is already sensitive to small changes in soil moisture content and amplification of these effects is not required.

FIG. 2. Electronic Circuit, one sensor

The manner of use of sensor 100 will be first described for the case of a house having three separate lawns each with an irrigation system controlled by clock timer 20 which controls three solenoid water switches 90a, 90b, 90c. Two different modes of use are available, depending on whether one sensor 100 is used for all three lawns or whether separate sensors 100a, 100b, 100c are used in each lawn. The case where one sensor 100 is used for all three lawns is described first. Sensor 100 is assumed to be a four electrode sensor 100 as shown in FIGS. 1a and 1b.

One of the lawns is selected for placement of sensor 100 and a location is found where the sprinklers place adequate water. This lawn, or lawn area, should be the last to be watered within the complete watering cycle. A small trench is dug into the lawn of sufficient size to allow sensor 100 to be placed horizontally into the trench. Typical trench dimensions for a lawn sensor are about six inches long, about four inches deep, and about one inch wide. Sensor 100 is placed horizontally in this small trench. It is desirable to surround sensor 100 with fine sand which provides an ideal medium for maintaining uniform contact between the soil, which may be lumpy, and the sensor. This is especially the case where the soil is rich in clay. It is much less important in sandy soils. Such an arrangement increases the sensitivity of sensor 100, while allowing excess water to drain away from sensor 100. The wires from sensor 100 are buried under the soil and lead to receiver 900 and transmitter 901.

When clock timer 20 switches power to one of the solenoids 90a, 90b and 90c, power also goes to transmitter 901. This power, which is an alternating current, is rectified by AC rectifier 30 and passes to relay 45 where it switches battery power on to AC constant current source 35, and also provides power to receiver 900. AC constant current source 35 provides an alternating current whose waveform is square and whose current magnitude is constant. This current goes to sensor 100. The amount of current required by sensor 100 depends on the resistivity of the ground in which sensor 100 is placed. Generally, from 10 microamps to a milliamp is required for household lawn conditions. The current passes from electrodes 14 on sensor 100 into the ground, penetrating the ground for some distance beyond sensor body 12. This current results in a square wave alternating voltage being produced across the other two wires on sensor 100. The voltage is fed into receiver 900, first passing into amplifier 50. The amount of amplification can be set with variable resistance 56 and this is called the wet point setting. The signal then passes to filter 55 to remove any sudden and undesired voltage surges and some of the 60 Hertz signals from local household electrical appliances. The signal then passes into AC to DC convertor 60 where it is converted to direct current. The signal is then input to comparator 65 whose variable resistance 66 allows the dry point setting to be made. The signal also goes to voltage display controller 70 which determines how many of the ten LED's it controls to turn on. Light emitting diode 68, coupled to the output of comparator 65, allows the state of the output of comparator 65 to be observed. When the signal input to the comparator reaches a level determined by the dry point setting variable resistance 66 the output from comparator 65 changes. The signal now goes to a device for setting delays 75. Two delays are used, one which allows several seconds to pass on startup so that all transient voltages decay to insignificance before usable measurements are taken. The second delay sets the amount of time which irrigation will continue, after sensor 100 indicates that the ground is sufficiently wet. This delay is called the run on time and is set by altering variable resistance 76. The signal then passes to electronic switch 85 and then to relay 80. A light emitting diode connected to electronic switch 85 monitors the output to solenoid 80 allowing its state to be observed. Electronic switch 85 senses the output changes from comparator 65 and, based on these changes, controls relay 80. When relay 80 switches to closed, the circuit containing the common wire from the clock timer to the solenoids is continuous and one of solenoids 90a, 90b and 90c is activated electrically, thus allowing water to pass through the irrigation pipes.

When clock timer 20 switches power to the second lawn irrigation system, transmitter 901, sensor 100 and receiver 900 are again activated, and will determine if irrigation is required. The same procedure takes place when clock timer 20 switches power to the third lawn irrigation system.

When the system is first installed, a setup procedure is required in order that wet and dry ground conditions are memorized by the electronics. To do this, the ground around sensor 100 is saturated with water and the wet point setting variable resistance 56 is adjusted until one or two light emitting diodes controlled by 70 are turned on. Another setting, called the dry point setting, is required when it is determined that the ground is sufficiently dry and watering is required. The dry point setting is controlled by variable resistance 66. This is set by observing light emitting diode 69 connected to electronic switch 85 which shows when solenoid switch 80 is closed. The third and final setting, called the run on time, is the amount of time that watering is to continue after sensor 100 indicates that sufficient water has been applied. This setting is controlled by variable resistance 76 connected to controllable delays 75. In the present embodiment of the system, the run on time can be set from two minutes to twenty minutes.

FIG. 3. Receiver Electronics

AC voltage from sensor 100 is input to amplifier 50. Part of amplifier 50 is a variable resistance 56 which is used to set the wet point setting. The signal then passes through a 0.2 microfarad capacitor and is then converted from AC to DC 60 and filtered 55. The signal is then fed into voltage display controller 70 which turns on up to 10 light emitting diodes, depending on the input signal and the gain setting of amplifier 50. The DC signal is then input to comparator 65 where it is compared to another voltage determined by variable resistance 66. This is used to set the dry point setting. When the signal input to comparator 65 is greater than the dry point setting voltage the output from comparator 65 switches to a high voltage (about 5 volts). Light emitting diode 68, coupled to the output from comparator 65 is turned on when the voltage from comparator 65 is low. This shows that the ground is sufficiently wet and no irrigation is required. From the output of comparator 65, the signal passes to controllable delays 75. The integrated circuit CD4538 is used to control two delays. The first delay is set to a few seconds, and allows all of the voltages to settle down when the system first switches on before measuring the voltage from sensor 100. The second delay determines the amount of time watering is to continue after sensor 100 indicates that the ground is wet. The signal next passes to electronic switch 85. This integrated circuit, number 74C74, switches two outputs mutually exclusively high or low depending on the input signal. Oscillator 82, (Integrated circuit CD4047) connected to 85, provides a clock pulse to drive 85. There are two outputs from 85. One goes to light emitting diode 69 and one goes to relay 80. Light emitting diode 69 indicates when the switched side of relay 80 is closed and hence watering is allowed.

FIG. 4. AC Constant Current Source

FIG. 4 shows one embodiment of the AC Constant Current source. AC power lines 25 are connected to AC rectifiers 30. When power is applied to any of the AC power lines 25, relay 45 closes and switches battery 40 power on. Constant current diode 36 then controls the amount of current which is output to sensor 100. Varying the resistance across constant current diode 36 allows the amount of current to be selected. Integrated circuits CD4066 61 and CD4047 62 produce alternating current at a frequency selectable by changing the values of the resistance and capacitance connected to 62. The constant alternating current is then passed to the current electrodes on sensor 100.

FIG. 5. Electronic Circuit, Three Sensors

When a different sensor 100*a*, 100*b*, 100*c* is placed in three different lawns, described under FIG. 2, each independent of the other, the installation is the same as for the single sensor 100 system. Setting the dry point, wet point and run on time will follow the procedure described under FIG. 2. In this system, one setting for the dry point and wet point will be used to control the irrigation for all three sensors. The operation of AC constant current source 35 and receiver 900 is described earlier.

FIG. 6. Four Wire System

FIG. 6 shows the manner of use when a four wire sensor 100 is used and is the case presented in the preceding descriptions. In this case, two wires from transmitter 901 are connected to sensor 100. Two wires are also connected from receiver 900 to sensor 100. The installation procedure and initial settings are completed, as described under the heading Electronic Circuit, One Sensor: FIG. 2.

FIG. 7. Three Wire System

FIG. 7 shows the manner of use when a three wire sensor 100 is used. In this case, one wire from transmitter 901 is grounded 86. The other wire is connected to sensor 100. The two wires from receiver 900 are connected to sensor 100. The installation procedure and initial settings are completed as described for the four wire sensor.

FIG. 8. Two Wire System

FIG. 8 shows the manner of use when a two wire sensor 100 is used. In this case, one wire from transmitter 901 is grounded 86, and one wire from the receiver 900 is grounded 87. The grounding for the transmitter 901 and receiver 900 should not be at the same point but should be separated by at least several feet. One wire from transmitter 901 is connected to sensor 100. One wire from receiver 900 is connected to sensor 100. The installation procedure and initial settings are completed as described for the four wire sensor 100.

FIGS. 9, 10, 11, 12 and 13, Tube Sensor and FIGS. 14 and 15, String Sensor

This section describes the manner of use of the tube sensor. The following remarks apply equally to the sensor 100. The tube sensor requires a current transmitter 901 and a voltage receiver 900, connected to the four metal tube electrodes as illustrated in FIG. 13. Two wires from the current transmitter 901 are connected to the metal tube current electrodes 201. In a typical tube sensor embodiment, each of the two current wires is connected to two adjacent metal tube electrodes 201, each with individual resistors 204 as illustrated in FIG. 13. Voltage receiver 900 is connected to the two remaining adjacent metal tube electrodes 201, as illustrated in FIG. 13. Other configurations of current transmitter 901 and voltage receiver 900 connections to the tube sensor are possible. For example, if current transmitter 901 wires are connected to nonadjacent metal tube electrodes 201, and the voltage receiver wires are connected to the remaining non adjacent metal tube electrodes 201, then very small voltages will generally be observed if the values of H, V1 and V2 are all equal. The tube sensor can be connected to the same transmitter 901 and receiver 900 circuits as were used for sensor 100. In addition, the tube sensor can be used with the four, three and two wire (tube) systems, as were described for sensor 100.

Increasing the length LN of the tube sensor, and hence the length of metal tube electrodes 201, increases the volume of soil which will influence the sensor. If two tube sensors 200 are used to measure a common region of soil moisture, then the tube sensor with the largest value of LN will have the lowest measured voltage. Since tube sensors 200 of all lengths have a common maximum voltage, when measurements are taken in air, the tube sensor with the larger value of LN will have the greatest range of voltage values for a common moisture measuring situation. However, since the measured voltage of a longer tube sensor can be small, more current may be required from current transmitter 901 in order to obtain a reasonable voltage magnitude.

In addition to measuring the moisture content changes of soil, the tube sensor is well suited to measuring moisture content changes in any granular medium, since the grains are free to surround the metal tube electrodes 201 for maximum effect. In addition, the metal tube sensor could be used for measuring the resistivity of liquids.

The tube sensor can be placed in soil to measure moisture content changes in several ways. Either a single tube sensor can be used or a string sensor, as illustrated in FIG. 14, can be used. In a typical tube sensor usage, the sensor is placed in a small amount of sand. Two typical orientations for placement of the sensor are horizontal and vertical. A horizontally placed tube sensor measures moisture content changes of a small region at the depth of the sensor. A vertically placed tube sensor measures the moisture content changes of a vertical region around the sensor. If the tube sensor is set vertically at a depth of only a few inches, then there is probably a significant difference in the moisture content changes over time at the shallow end of the tube sensor compared with those at the deep end of the tube sensor. The vertically set tube sensor measures an average of these different moisture content changes.

Another way to measure an average of moisture content changes at both a shallow depth and at a deeper depth is to use a string sensor as shown in FIGS. 14 and 15. A typical string sensor for these measurements may contain two serially arranged tube sensors. One sensor of the tube sensor on the string is placed, in sand, at a shallow depth. The second tube sensor on the string is placed at a deeper location. In a typical setting such as this, the sensors would be placed horizontally. However, they could also be placed vertically.

If one sensor on a string of sensors (string sensor) is placed in a dry location and another identical sensor on the same string is placed in a wet location, the measured voltage output is dominated by the sensor in the wet location. This situation can be changed by increasing the length of the sensor in the dry location. Increasing the length of the sensor will lower the measured voltage for a particular soil dryness. The sensor length should ideally be lengthened until its measured voltage is about the same as the measured voltage from the sensor in the wet area.

In practice, one of the sensors of a string of sensors may be about 10 cm in length, and the other sensor may be about 20 cm in length. In this case, the longer sensor is placed in the dryer region and the shorter sensor is placed in the wetter region.

The above description and operation has shown that sensor 100, transmitter 901 and receiver 900 are able to perform the numerous objects and advantages described earlier. For example, sensor 100 is able to respond to small soil moisture changes, and to respond instantaneously. More importantly, sensor 100 can be made to respond to a desired volume of soil and can thus be focused at the well defined depth of grass roots. Sensor 100 can be manufactured inexpensively and is durable. Measurements are independent of any electrochemical voltages which may occur at the electrode to soil interfaces. Receiver 900 allows the user to determine the correct soil moisture conditions before irrigation is to occur, along with the degree of saturation when irrigation stops.

Constant irrigation over many years can lead to a build up of salts in the soil. This will result in a lowering of the soil resistivity and hence the measured voltages. Sensor 100 and receiver 900 can be used to monitor this lowering of the soil resistivity and hence monitor long term soil salinity changes.

While the above description contains many of the specifics, these should not be construed as limitations on the scope of the invention, but rather as an exemplification of preferred embodiments thereof. Many other variations are possible. For example, sensors are not limited to a cylindrical shape. Nor is the number of electrodes limited to four or less, as described. More electrodes could be used for different measuring schemes. In addition, the sensor could be coated with a porous material, such as a porous ceramic, or porous plastic, having specifically designed wicking properties. This allows the sensor to respond to different kinds of soils with different pore pressures. The value of T can be modified to select the contribution that this porous material makes to the measured voltage. In this case, a large value of T concentrates the influence of the sensor to the thin coating. Different materials could be used for the electrodes. The electronic controls could be designed in many different ways. For example, a different wet and dry point setting could be set for each sensor, as well as a different current magnitude to each sensor. Digital electronics could be used, and moisture changes displayed using a liquid crystal display. Several sensors can be placed at different locations in an area of interest. These sensors can be coupled in series thereby providing a better average soil moisture indicator.

Thus, the scope of the invention should be determined by the appended claims and their legal equivalent, rather than by the examples given.

What is claimed is:

1. A method of measuring soil moisture, comprising;

providing a moisture content sensor having a first and a second rigid and electrically insulating body member, said first and second body members being physically spaced apart to define a sensor length parameter and to define an open space between said first and second body members, a plurality of electrically uninsulated and rigid electrical electrodes, each of said electrodes having a first end and a second end, said first end of each electrode being mechanically fastened to different physically spaced points on said first body member, said electrodes passing between said first and second body members in a manner such that said electrodes do not physically touch, and said second ends of each electrode being mechanically fastened to different physically spaced points on said second body member, said plurality of electrodes thereby forming a unitary physical assembly with said first and second body members having said open space between said first and second body members, connecting current transmitter means to one of said ends of first ones of said electrodes, connecting voltage receiver means to one of said ends of different second ones of said electrodes, said voltage receiver means providing an output indicative of moisture content, and placing said sensor in soil whose moisture content is to be measured.

2. The method of claim 1 including the step of;

selecting said plurality of electrodes from the group two, three and four electrodes.

3. The method of claim 2 including the step of;
providing said current transmitter means as an oscillating current transmitter means.

4. The method of claim 3 including the step of;
providing said oscillating current transmitter means as a constant oscillating current transmitter means.

5. The method of claim 1 wherein said electrodes are metal electrodes selected from the group hollow metal rods and solid metal rods.

6. The method of claim 2 including the step of;
coating said metal electrodes with an electrically conductive material selected to protect said metal electrodes from chemical effects present in soil.

7. The method of claim 2 including the steps of;
providing said first ones of said metal electrodes as cylindrical rods having a relatively small diameter, and
providing said different second ones of said metal electrodes as cylindrical rods having a relatively large diameter.

8. The method of claim 1 wherein said plurality of electrodes comprise an even number, and including the step of;
connecting electrical resistance means between pairs of said first ones and said different second ones of said electrodes.

9. The method of claim 1 including the step of;
providing a plurality of said sensors, said plurality of sensors including a first sensor and a last sensor,
connecting said first ones of said electrodes within said plurality of sensors in electrical series circuits,
connecting said current transmitter means to said one end of said first ones of said electrodes that are within said first sensor,
connecting said different second ones of said electrodes within said plurality of sensors in electrical series circuits,
connecting voltage receiver means to said one end of said different second ones of said electrodes that are within said first sensor, said voltage receiver means providing an output indicative of moisture content, and
placing said plurality of sensors in soil whose moisture content is to be measured.

10. The method of claim 9 wherein said electrodes are metal electrodes selected from the group hollow metal rods and solid metal rods.

11. The method of claim 10 wherein said plurality of electrodes within said plurality of sensors comprise the same even number of electrodes within each of said sensors, and including the step of;
connecting electrical resistance means between pairs of said first ones and said different second ones of said electrodes within said last sensor.

12. The method of claim 11 including the steps of;
providing said first ones of said metal electrodes as cylindrical rods having a relatively large diameter, and
providing said different second ones of said metal electrodes as cylindrical rods having a relatively small diameter.

13. The method of claim 12 including the step of;
coating said metal electrodes with an electrically conductive material selected to protect said metal electrodes from corrosive chemical effects present in soil.

14. A device adapted for the measurement of soil moisture, comprising;
a first and a second rigid and electrically insulating body member, said first and second body members being physically spaced apart to define a physically open soil volume therebetween,
first, second, third and fourth electrically uninsulated and rigid electrodes, each of said four electrodes having a first end and a second end,
means fastening said first ends of each of said four electrodes to different physically spaced points on said first body member in the sequence first, second, third and fourth electrode,
said four electrodes then passing through said open space between said first and second body members in a manner such that said four electrodes do not physically touch,
means fastening said second ends of each of said four electrodes to different physically spaced points on said second body member in the sequence first, second, third and fourth electrode, to thereby form a unitary assemble with said first and second body members wherein said four electrodes occupy only a portion of said open soil volume,
current transmitter means connected to first body member and to said first ends of first and second electrodes, and
voltage receiver means connected to said first body member and to said first ends of said second and third electrodes, said voltage receiver means providing an output indicative of soil moisture content.

15. The device of claim 14 wherein said current transmitter means is an oscillating current transmitter means.

16. The device of claim 15 wherein said oscillating current transmitter means is a constant oscillating current transmitter means.

17. The device of claim 14 wherein said electrodes are metal electrodes selected from the group hollow metal rods and solid metal rods.

18. The device of claim 14 wherein said first and second electrodes are cylindrical rods having a relatively large diameter, and said third and fourth electrodes are cylindrical rods having a relatively small diameter.

19. The device of claim 18 including an external surface coating on said metal electrodes of an electrically conductive material selected to protect said metal electrodes from chemical effects present in soil.

20. The device of claim 14 including;
first resistance means connected from said second end of said first electrode to said second end of said fourth electrode, and
second resistance means connected from said second end of said second electrode to said second end of said third electrode.

21. A device adapted for the measurement of soil moisture, comprising;
a plurality soil moisture sensors, each sensor having
a first and a second rigid and electrically insulating body member, said first and second body members being physically spaced apart to define an open space therebetween,
first, second, third and fourth electrically uninsulated and rigid electrodes, each of said electrodes having a first end and a second end,
means fastening said first ends of each of said four electrodes to different physically spaced points on said first body member in the sequence first, second, third and fourth electrode, with successive electrodes being adjacent to each other, said four electrodes then passing between said first and second body members in a manner such that said four electrodes do not physically touch, and means fastening said second ends of each of said four electrodes to different physically spaced points on said second body member in the sequence first, second, third and fourth electrode, to thereby form a unitary assemble of said four conductors and said first and second body members with said open space being between said first and second body members, first circuit means connecting said first electrodes of said plurality of sensors in a series circuit from a first sensor to a last sensor, second circuit means connecting said second electrodes of said plurality of sensors in a series circuit from said first sensor to said last sensor, third circuit means connecting said third electrodes of said plurality of sensors in a series circuit from said first sensor to said last sensor, fourth circuit means connecting said fourth electrodes of said plurality of sensors in a series circuit from said first sensor to said last sensor, current transmitter means connected to said first sensor and to said first ends of first and second electrodes at said first body member thereof, and voltage receiver means connected to said first sensor and to said first ends of said third and fourth electrodes at said first body member thereof.

22. The device of claim 21 wherein said current transmitter means is an oscillating current transmitter means.

23. The device of claim 22 wherein said oscillating current transmitter means is a constant oscillating current transmitter means.

24. The device of claim 21 wherein said electrodes of said plurality of sensors are selected from the group hollow metal rods and solid metal rods.

25. The device of claim 21 wherein said first and second electrodes are cylindrical metal rods having a relatively large diameter, and wherein said third and fourth electrodes are cylindrical metal rods having a relatively small diameter.

26. The device of claim 25 including an external surface coating on said electrodes of a material selected to chemically protect said electrodes.

27. The device of claim 21 including;

first resistance means connected to said first and second electrodes at a position spaced from said first sensor, and second resistance means connected to said third and fourth electrodes at a position spaced from said first sensor.

28. The device of claim 21 including;

first resistance means connected to said last sensor and to said second ends of said first and fourth electrodes at said second body member thereof, and second resistance means connected to said last sensor and to said second ends of said second and third electrodes at said second body member thereof.

29. A device adapted for the measurement of soil moisture, comprising;

a first and a second rigid body member, said first and second body members being physically spaced apart to define a physically open soil volume therebetween for occupancy by soil, a plurality of electrically uninsulated and rigid electrodes, each of said electrodes having a first end and a second end, means fastening said first ends of each of said plurality of electrodes to different physically spaced points on said first body member and in a given sequence, said plurality of electrodes passing between said first and second body members in a manner such that said four electrodes do not physically touch, in a manner to leave said open soil volume generally unobstructed for said occupancy by soil, and means fastening said second ends of each of said plurality of electrodes to different physically spaced points on said second body member and in said given sequence.

30. The device of claim 29 wherein said plurality of electrodes is selected from the group two, three or four electrodes.

31. The device of claim 29 wherein said electrodes are generally parallel metal electrodes selected from the group hollow metal rods and solid metal rods.

32. The device of claim 31 wherein said plurality of electrodes comprise a first group of metal rods having a relatively large cross sectional area, and a second group of metal rods having a relatively larger cross sectional area.

33. The device of claim 31 including an external surface coating on said metal rods of an electrically conductive material selected to protect said metal electrodes from chemical effects present in soil.

34. The device of claim 29 wherein said plurality of electrodes comprise an even number X of electrodes, and including;

X/2 resistance means, one of said resistance means being connected from said second end of an electrode in said first group to said second end of an electrode in said second group.

35. The device of claim 29 including;

a plurality of resistance means, one of said resistance means being connected from said second end of an electrode in said first group to said second end of an electrode in said second group.

36. A device adapted for the measurement of soil moisture, comprising;

a plurality soil moisture sensors, each sensor having a first and a second rigid and electrically insulating body member, said first and second body members being physically spaced apart to define an open space therebetween for occupancy by soil, a plurality of electrically uninsulated and rigid electrodes, each of said electrodes having a first end and a second end, means fastening said first ends of each of said plurality of electrodes to different physically spaced points on said first body member in the sequence from a first of said plurality to a last of said plurality, said plurality of electrodes then passing through a portion of said open space between said first and second body members in a manner such that said electrodes do not physically touch, and means fastening said second ends of each of said plurality of electrodes to different physically spaced points on said second body member in the said sequence, to thereby provide a remainder of said open space to be occupied by soil, and to thereby form said plurality of electrodes and first and second body members into a unitary physical assembly, and a plurality of means connecting said electrodes of said plurality of sensors in a plurality of series circuit from a first sensor to a last sensor.

37. The device of claim 36 wherein said electrodes of said plurality of sensors are selected from the group hollow metal rods and solid metal rods.

38. The device of claim 37 wherein certain ones of said plurality of electrodes are cylindrical metal rods having a relatively large diameter, the remainder of said plurality of electrodes being cylindrical metal rods having a relatively small diameter.

39. The device of claim 38 including an external surface coating on said electrodes of a material selected to chemically protect said electrodes.

40. A plural-sensor device adapted for the measurement of soil moisture, comprising;

a plurality of soil moisture sensors, each of said sensors having rigid electrically insulating first and second body members that are physically spaced apart to define an open space therebetween, a plurality of electrically uninsulated electrodes, each of said electrodes having a first end and a second end, means fastening said first ends of each of said plurality of electrodes to different physically spaced points on said first body member in a sequence from a first of said plurality of electrodes to a last of said plurality of electrodes, said plurality of electrodes then passing through a first portion of said open space between said first and second body members in a manner such that said electrodes do not physically touch, and means fastening said second ends of each of said plurality of electrodes to different physically spaced points on said second body end in said sequence, to thereby form said plurality of electrodes and said first and second body members into a unitary assembly having a second portion of said open space that is unoccupied by said plurality of electrodes, and a plurality of electrical connection means connecting said electrodes of said plurality of sensors in a plurality of series circuits from a first of said plurality of sensors to a last of said plurality of sensors.

41. The device of claim 40 including an external surface coating on said electrodes of a material selected to protect said electrodes from chemical effects within the soil.

42. The device of claim 40 including;

a first pair of electrical conductors at said first sensor connected to a first group of said plurality of electrodes at said first sensor, said first pair of electrical conductors being adapted to be connected to current transmitter means, and a second pair of electrical conductors at said first sensor connected to a second group of said plurality of electrodes at said first sensor, said second pair of electrical conductors being exclusive of said first pair of electrical conductors, and said second pair of electrical conductors being adapted to be connected to voltage receiver means.

43. The device of claim 42 including;

a plurality of resistance means at one of said plurality of sensors exclusive of said first sensor, each individual one of said resistance means being connected from one of said first group of electrodes to one of said second group of electrodes.

* * * * *